United States Patent [19]

Clegg et al.

[11] Patent Number: 4,823,808

[45] Date of Patent: Apr. 25, 1989

[54] METHOD FOR CONTROL OF OBESITY, OVERWEIGHT AND EATING DISORDERS

[76] Inventors: Charles T. Clegg, 1418 Thayer Ave., Los Angeles, Calif. 90024; Garn A. Wallace, 1647 Manning Ave., Los Angeles, Calif. 90024

[21] Appl. No.: 70,178

[22] Filed: Jul. 6, 1987

[51] Int. Cl.⁴ ............................................. A61B 7/00
[52] U.S. Cl. .................................... 128/773; 128/748; 128/780; 128/903; 128/905
[58] Field of Search ............................ 128/773–774, 128/780, 782, 748, 903, 905

[56] References Cited

U.S. PATENT DOCUMENTS

| | | | |
|---|---|---|---|
| 3,480,003 | 11/1969 | Crites | 128/748 |
| 3,672,352 | 6/1972 | Summers | 128/773 X |
| 3,858,575 | 1/1975 | Rose | 128/773 X |
| 3,939,823 | 2/1976 | Kaye et al. | 128/748 |
| 4,063,550 | 12/1977 | Tiep | 128/905 X |
| 4,461,301 | 7/1984 | Ochs | 128/905 X |
| 4,571,750 | 2/1986 | Barry | 128/773 X |
| 4,592,342 | 6/1986 | Salmasian | 128/1 R |

FOREIGN PATENT DOCUMENTS

| | | | |
|---|---|---|---|
| 2925699 | 1/1981 | Fed. Rep. of Germany | 128/903 |
| 2459648 | 2/1981 | France | 128/773 |
| 0178028 | 2/1966 | U.S.S.R. | 128/780 |
| 0641957 | 1/1979 | U.S.S.R. | 128/773 |
| 0733638 | 5/1980 | U.S.S.R. | 128/748 |

Primary Examiner—Kyle L. Howell
Assistant Examiner—Angela D. Sykes
Attorney, Agent, or Firm—Terry M. Crellin

[57] ABSTRACT

Methods for the treatment of obesity, overweight, compulsive overeating, emotional overeating, binge eating, bulimia and anorexia comprises the steps of monitoring physiological parameters in the esophageal and/or gastrointestinal tract which are associated with gastric relaxation, gastric filling, gastric contractions, gastric secretions, and gastric emptying. The measurement are transmitted either directly to a receiver or via radiotelemetry to a receiver. The receiver has a data processor associated therewith, and the data processor produces audio and/or visual feedback for the person under treatment to hear and/or see. This feedback is used for purposes of teaching behavior modification and other psychotherapeutic purposes. In the most simple form of the invention, a warning sound is generated by the data processor indicating when sufficient food has been ingested. This warning can be generated by the monitoring apparatus much sooner than the biological signal of fullness transmitted by the stomach to the brain of the person. The person can thereby discontinue eating before otherwise becoming unconsciously too full.

20 Claims, No Drawings

METHOD FOR CONTROL OF OBESITY, OVERWEIGHT AND EATING DISORDERS

BACKGROUND OF THE INVENTION

1. Field of the Invention

The present invention relates generally to methods for the control of obesity, overweight, and eating disorders, including anorexia, bulimia, and compulsive overeating. In particular, the invention relates to methods for sensing the quantity of food consumed and/or the monitoring of various physiological changes during food ingestion and digestion, with the monitored data being presented visually or through auditory means or other sensations to a person who is participating in a program of treatment involving voluntary limitation of dietary intake and/or behavior modification.

2. State of the Art

Obesity has been treated in many ways, with the overall goal being to reduce ingestion below energy expenditure so as to result in a weight loss. Energy expenditure is increased by physical activity increases, and the physical activity further results in an increase in metabolic rate lasting beyond the period of exercise. Energy intake is reduced through dietary restriction or other means. Numerous theories exist regarding various topics which are believed to influence body weight, such as genetics, fat cell number behavior, and developmental psychology. Finally systems theory has also been used to partially account for difficulties with overweight, obesity, and eating disorders.

Currently used treatments for obesity and overeating include psychological interventions, dietetics, exercise, gastric balloons, stomach staping, jaw wiring, surgery, drugs and behavior modifications. An important of the psychological interventions may also include assessment and treatment of body image. Behavior modification, including assessment and treatment of body image, is a most effective treatment when combined with diet and exercise.

Behavior modification in its broadest sense includes several basic routines. With respect to diet, both portion size and type of food ingested is controlled. Behavior surrounding eating, from shopping, to the time, place and method of eating, is controlled. Cognitive restructuring is directed at changing attitudes and maladaptive beliefs about the self, food, and eating. Increased physical activity is encouraged, and psychotherapy is used to support behaviour change and/or induce emotional change and understanding. Body image is frequently assessed, and education is used through the process, including significant dietetic, medical, and psychological information.

Biofeedback has only little been used in treatment of eating behavior, and then only in the most elemental form. Self monitoring, which is a primitive form of biofeedback, is a mainstay of behavior modification. Patients on diets are encouraged to not wear loose-fitting clothing, and occasionally it is recommended that cords be put around the patients abdomen to detect increasing or decreasing girth. Weighing on a scale is another elemental form of biofeedback. More developed forms of biofeedback have been used in other areas of medical treatment but not for the treatment of overeating and obesity. For example, biofeedback or psychotherapeutic treatment have been suggested for controlling physiological or psychophysiological variables not ordinarily sensed by individuals.

It has also been recognized that many overeaters confuse emotional and other cues for hunger and eat because of anxiety or other emotional states. Some treatment programs have patients become hungry and then eat small amounts of food in a controlled setting in an effort to detect feelings of fullness or the effects of food entering the stomach and to differentiate these sensations from the various forms of emotional tension which may also coincidentally be present. The attempt is made to get overeaters to pay attention to bodily signals as opposed to emotions as cues to eat.

3 OBJECTIVES

A principal objective of the invention is to provide an advantageous technique utilizing specially developed forms of biofeedback in a treatment for obesity and overeating.

A particular objective of the invention is to provide a biofeedback system and process wherein physiological parameters are measured from any of various positions along the esophageal and/or the gastrointestinal tract, wherein the measured parameters are used to develop audio and/or visual analog signals for psychotherapeutic treatment of obesity, overweight and eating disorders, especially bulimia.

Another objective of the present invention is to provide a relatively inexpensive method for psychotherapeutic treatment of obesity, overweight, and eating disorders, especially bulimia, wherein autio and/or visual analog signals corresponding to physiological parameters measured along the esophageal and/or gastrointestinal tract are used as reinforcement signals to alert the patient of natural cues or sensations which the patient may otherwise consciously or unconsciously ignore.

BRIEF DESCRIPTION OF THE INVENTION

The above objectives are achieved in accordance with the present invention by providing novel, unique methods for the treatment of obesity, overweight, compulsive overeating, emotional overeating, binge eating, bulimia, anorexia and hypertension associated with weight loss. The methods of the present invention function through the mechanism of measuring physiological parameters in the esophageal and/or gastrointestinal tract which are associated with gastric relaxation, gastric filling, gastric contractions, gastric secretions, and gastric emptying. Gastric pressure from distention, sounds from peristalsis of the gastrointestinal and esophageal tract, pH changes from secretions, temperature changes from the bolus of food or liquid, hunger sensations from smooth muscle activity, etc., are transmitted either directly to a receiver or via radiotelemetry to the receiver. The receiver is associated with a data processor. The data processor is used to interpret the measurements and/or to display the measurements or interpretations thereof for purposes of teaching behavior modification and othe psychotherapeutic purposes. Voluntary gastric musculature control can be learned through visual and auditory means which are generated by the processor. In addition, computer-generated graphics can be used in the psychotherapeutic treatment. The devices used to measure the physiological parameters can either be positioned on the body of the person being treated or they can be of the type which are swallowed or inserted within the gastrointestinal tract. The internal dwelling devices can be restricted to the stomach of the person being treated with the aid of a gastric bubble or balloon.

Additional objects and features of the invention will become apparent from the following detailed description.

DETAILED DESCRIPTION OF THE PREFERRED EMBODIMENTS

When food is consumed, the stomach distends, and the distended stomach transmits a neural signal to the brain indicating that the stomach is full and no further intake of food is needed or desirable. Unfortunately, conscious awareness of this signal commonly occurs only after 15 to 20 minutes after eating. The present invention utilizes biofeedback means to apprise the eater of the indication of fullness much more rapidly, and in essence virtually instantaneously with the filling of the stomach.

In developing the biofeedback, physiological data such as pressure measured in the stomach and/or sounds generated in the esophageal and gastrointestinal tracts are advantageously used. Two systems of monitoring such physiological data are possible. One such system comprises an external means of monitoring sound developed in the esophageal and gastrointestinal tracts. The other system uses an indwelling device to monitor pressure and sounds generated in the gastrointestinal tract and especially the stomach. Each of these two systems will be described separately hereinafter.

The system using the external means of monitoring sound in the esophageal and gastrointestinal tracts comprises a microphone which is mounted on the person's body by means of adhesive, adhesive tape or patch, belt, elastic bands, or other external contrivance. Ordinary mounting positions include the epigastric region, the upper abdomen, over the pylorus externally, or in an esophageal position on the anterior neck near the thyroid. The microphone can also be placed on the person's cheek or under the jaw to monitor chewing.

The sounds measured by the microphone are transmitted to a data processor which produces an auditory analog signal. The data processor may be a specially built computer and the microphone can be connected to the data processor by a direct wire hookup or the microphone could include a radio transmitter, whereby the sounds monitored by the microphone are transmitted by radiotelegraphy to the data processor. Preferably, the microphone has an FM transmitter associated therewith which transmits the sound data monitored by the microphone to a receiver which is associated with the data processor.

In the most simple construction, the data processor is a basic sound amplifier which amplifies the measured sound for the person under treatment to hear. This gives the person a clear, audible feedback of esophageal or gastrointestinal sound. In a more complex system, the data processor produces auditory analog signals of variable tones or pitches representing different levels of esophageal and gastrointestinal sound. The data processor can in effect simply add the amount of sound monitored or the time period of monitoring sound to determine when the stomach is full. As the sound is monitored, the tone or pitch of the sound produced for the person under treatment to hear changes to give the person an indication of the amount of food consumed. When the stomach is full, the data processor can produce an exceptionally loud or piercing sound to alert the person that it is time to stop eating.

The data processor could be connected to an FM receiver worn on the ear or other place on the body, with an amplifier producing sound available to the auditory canal of the person under treatment. As the total volume of sound produced in eating increases to a certain point, the computer or data processor would increase the tone or volume of sound to warn the individual that overeating has occurred. In this sense, overall meal sound could be converted to a tone or digital readout available to the person under treatment to prevent overeating or under-eating. Such volumetric analysis may indicate internal pressure increases in the stomach which are not immediately sensed by an overeater, or bulimic. This gives the person under treatment an awareness of fullness before subjective awareness would otherwise occur without the biofeedback. As mentioned previously, normal fullness is sensed subjectively in about 15 to 20 minutes. With the biofeedback system of the present invention, a signal would be produced much sooner, warning the person of potential discomfort or unwarranted eating behavior. The sound heard by the individual could be the actual sound from the esophageal or gastrointestinal tracts, a warning buzzer or tone, or an artificial sound produced by the data processor.

The data processor or computer can be programmed to analyze the data and to display pressure curves or gastric volume based on the monitored data. The computer can display animated scenes in real time of what is occurring within the stomach or gastrointestinal tract, as well as provide display of all measured data. The animated cartoon scenes may be representational of what has actually occurred, or may be simply cartoon approximations.

The computer program can be part of an overall treatment program. Such a treatment program would also include the use of various 24-hour or longer monitoring recorders. These monitoring recorders might be worn by an individual and record eating activity from the external sensor for periods of time, such as hourly, daily, weekly or monthly. This data, once recorded, can be used to teach bahavior modifications and to educate a person about the relationship between time of day, gastric activity and eating habits. In addition, emotional responses as they are perceived by the person can be integrated with the available recorded data.

In the behavior modification program, the data and output of the data processor would be used to indicate internal cues to a person as he or she eats. The behavior modification program would include slow eating, steps to differentiate emotions from hunger in a clinical setting, and cognitive therapies to connect the physiologic measurements to words in various statements. Beyond that, the individual in treatment could learn to differentiate emotions from physiological occurrences, and the person could be taught the relationship between emotion and physiological occurrences through the use of biofeedback.

The system of the present invention could have educational functions about normal physiological processes and digestive processes. The data obtained through a computer, or other data processor, permits conceptual formation in an individual which ordinarily might not be present without using the present system. Data is made available to an individual which might not be sensed or understood to be present by a person consciously without the use of the present system. Psychotherapy can be assisted through the use of the present system. For example, a person unaware of a particular emotion, affect, or fantasy might have a physiological response picked up by the microphone and recognized by the computer. Biofeedback could be given directly to the person. A treating therapist would then clarify what it is the person might be feeling emotionally, outside of his ordinary awareness, but picked up physiologically by the microphone. Therefor, physiologic clues could be used to detect emotions, and unconscious affects manifested only in physical measurement could be registered consciously and cognitively.

The system using the indwelling monitoring means is very similar to the system previously described which utilizes an external means of monitoring sound in the esophageal and gastrointestinal tracts, with the principal exception being that an indwelling monitoring means is used rather than an external means. The indwelling monitor comprises a radiotelemetry capsule which is adapted to monitor or measure those parameters which are desired. The indwelling monitor can be made to measure such parameters as pressure, sound, temperature and presence or absence of selected chemicals such as electrolytes, hormones, blood, and bacteria. The monitor further includes a transducer which emits a radio signal, preferably a low-power, frequency modulated, radio signal, representative of the parameters being measured. Measurements of multiple parameters can be sent on separate, multiple radio frequencies, or such multiple signals can be multiplexed and transmitted on a single frequency.

The indwelling monitor can be placed in the gastrointestinal tract several different ways. It can be inserted in the stomach with a gastric balloon, wherein it may reside in the wall of the gastric balloon. It can be surgically implanted in the gastric wall, or it may be swallowed or ingested. When ingested, the monitor would travel through the gastrointestinal tract if it were not fixed in position. It can be fixed in position by restricting its onward passage using either an attached thread passing from the device through the esophageal tract to the mouth of the person. The thread or tether is attached to a tooth or to the skin on the cheek.

The system utilizing the indwelling monitor functions through the same basic mechanism as the previously described system comprising the external monitor. The indwelling monitor measures physiological parameters in the gastrointestinal tract, and the measurements are transmitted by radio signals to the data processor. Auditory or visual signals can be generated by the data processor which relate directly to the measured parameters, or the data processor can analyze the measured signals and produce appropriate visual or auditory feedback for the person who is being treated. The operation of the data processor is identical with that described previously with relation to the system comprising the external monitor.

Although preferred embodiments of the methods and systems of the present invention have been illustrated and described, it is to be understood that the present disclosure is made by way of example and that various other embodiments are possible without departing from the subject matter coming within the scope of the following claims, which subject matter is regarded as the invention.

We claim:

1. A method for the treatment of obesity, overweight, compulsive overeating, emotional overeating, binge eating, bulimia, anorexia and hypertension associated with weight loss, said method comprising
   measuring gastrointestinal sound in a person under treatment while the person is eating or drinking;
   transmitting the measured sound to a data processor which produces an auditory analog signal;
   amplifying the auditory analog signal; and
   reproducing the auditory analog signal for the person under treatment to hear, thus giving the person under treatment a clear, audible feedback of gastrointestinal sound.

2. A method in accordance with claim 1, wherein the data processor produces auditory analog signals of variable tones or pitches representing different levels of gastrointestinal sound indicating the presence and rate of gastric filling.

3. A method in accordance with claim 1, wherein the gastrointestinal sound is measured using a radiotelemetry capsule which is placed in the stomach of the person under treatment, with the radiotelemetry capsule comprising a sound sensitive transducer and means for emitting a low power, frequency modulated, radio signal corresponding to gastric sound, and further wherein a receiver is placed near the stomach on the exterior of the body of the person under treatment, and the receiver receives the radio signal from the radiotelemetry capsule and forwards the radio signal on to said data processor.

4. A method in accordance with claim 3, wherein the radiotelemetry capsule is constrained to the stomach of the person under treatment.

5. A method in accordance with claim 3, wherein the data processor in combination with display means produces a visual display of animations or cartoons from the measured sounds, with the animations or cartoons representing gastric filling and function during eating and drinking.

6. A method in accordance with claim 3, wherein the data processor also produces a signal which is displayed on a visual display means such as a meter or video monitor.

7. A method in accordance with claim 1, wherein the data processor also produces a signal which is displayed on a visual display means such as a meter or video monitor.

8. A method in accordance with claim 1, wherein the data processor in combination with display means produces a visual display of animations or cartoons from the measured sounds, with the animations or cartoons representing gastric filling and function during eating and drinking.

9. A method in accordance with claim 1, wherein the data processor produces auditory analog signals of variable tones or pitches representing the total volume of sound produced and the total volume of gastric filling from ingestion over a particular period of time.

10. A method in accordance with claim 1, wherein the data processor comprises a computer and a microphone is placed against the body of the person under treatment to monitor gastric sounds.

11. A method in accordance with claim 1, wherein the data processor comprises a computer and a microphone is placed against the esophageal tract of the person under treatment to monitor swallowing or chewing sounds and the sounds of food or liquid as it passes from the mouth through the esophagus and into the stomach.

12. A method for the treatment of obesity, overweight, compulsive overeating, emotional overeating, binge eating, bulimia, anorexia and hypertension comprising measuring gastrointestinal pressure in a person under treatment while eating or drinking;

transmitting the measured pressure to a data processor which produces an auditory analog signal; and amplifying the auditory analog signal and reproducing the auditory analog signal for the person under treatment to hear giving the person under treatment a clear audible feedback of gastrointestinal pressure.

13. A method in accordance with claim 12, wherein the data processor produces auditory analog signals of variable tones or pitches representing different levels of gastrointestinal pressure indicating the presence and rate of gastric filling.

14. A method in accordance with claim 12, wherein the data processor in combination with display means produces a visual display of animations or cartoons from the measured sounds, with the animations or cartoons representing gastric filling and function during eating and drinking.

15. A method in accordance with claim 12, wherein the data processor also produces a signal which is displayed on a visual display means such as a meter or video monitor.

16. A method in accordance with claim 12, wherein the gastrointestinal pressure is measured using a radiotelemetry capsule which is placed in the stomach of the person under treatment, with the radiotelemetry capsule comprising a pressure sensitive transducer and means for emitting a low power, frequency modulated, radio signal corresponding to gastric pressure, and further wherein a receiver is placed near the stomach on the exterior of the body of the person under treatment, and the receiver receives the radio signal from the radiotelemetry capsule and forwards the radio signal on to said data processor.

17. A method in accordance with claim 16, wherein the radiotelemetry capsule is constrained to the stomach of the person under treatment.

18. A method in accordance with claim 16, wherein the data processor in combination with display means produces a visual display of animations or cartoons from the measured sounds, with the animations or cartoons representing gastric filling and function during eating and drinking.

19. A method in accordance with claim 16, wherein the data processor also produces a signal which is displayed on a visual display means such as a meter or video monitor.

20. A method in accordance with claim 16, wherein the data processor comprises a computer, and the method further comprises placing a pressure sensing element in the stomach of the person under treatment to monitor gastric pressure.

* * * * *